United States Patent
Bartkiewicz

[11] Patent Number: 5,900,547
[45] Date of Patent: May 4, 1999

[54] DIFFERENTIAL LEVEL HYDROMETER

[75] Inventor: Luke Bartkiewicz, Gautier, Miss.

[73] Assignee: ThermoProbe Inc., Jackson, Miss.

[21] Appl. No.: 08/928,650

[22] Filed: Sep. 12, 1997

[51] Int. Cl.$^6$ .................................................. G01N 9/10
[52] U.S. Cl. ................................................ 73/447; 73/32 R
[58] Field of Search ............................ 73/447, 444, 448, 73/449, 450, 451, 32 R, 293, 437; 250/903

[56] References Cited

U.S. PATENT DOCUMENTS

| | | | |
|---|---|---|---|
| 576,537 | 2/1897 | Barry | 73/444 |
| 1,524,928 | 2/1925 | Hardel et al. | 73/450 |
| 2,496,447 | 2/1950 | Dresser | 73/293 |
| 3,895,235 | 7/1975 | Melone | 250/577 |
| 3,921,461 | 11/1975 | Layton | 73/447 |
| 4,000,657 | 1/1977 | Ponsar | 73/448 |
| 4,075,770 | 2/1978 | Lill | 73/448 |
| 4,240,282 | 12/1980 | Nelson | 73/447 |
| 4,400,978 | 8/1983 | Guay et al. | 73/453 |
| 4,501,972 | 2/1985 | Foerster, Jr. et al. | 250/577 |
| 4,745,293 | 5/1988 | Christensen | 250/577 |
| 4,904,878 | 2/1990 | Gipp et al. | 250/577 |
| 4,962,395 | 10/1990 | Baird | 73/293 |
| 4,994,682 | 2/1991 | Woodside | 250/577 |
| 5,209,106 | 5/1993 | Carlin | 73/49.2 |
| 5,235,179 | 8/1993 | Chang et al. | 250/227.21 |

OTHER PUBLICATIONS

Plummer, *Marine Services Inc.*, "Laboratory Method of Viewing Miniscus," 3 pages (undated).
*Gravity*, 4 pages (undated).
*Specific Gravity Homework*, "Specific Gravity & Soft Drinks," 2 pages, Revised Jul. 22, 1996, Web Site: www.c-ci.unl.edu/SHU/SpGravityHW.html, Accessed on Jul. 29, 1997.

*Primary Examiner*—John E. Chapman

[57] ABSTRACT

A differential level hydrometer reduces the possibility for user error and provides an accurate, predictable, easy to use, reliable instrument for measuring the density (specific gravity) of a liquid. The differential level hydrometer works by automatically measuring the level of a liquid within a vessel and floating, in the liquid, a calibrated float having a precisely known volume and density. The instrument automatically measures the level of the liquid within the vessel while the float is floating in the liquid, and automatically calculates the density (specific gravity) of the liquid based on the two measured levels and the volume and density of the float. Temperature and meniscus correction may be used to improve repeatability and accuracy.

19 Claims, 5 Drawing Sheets

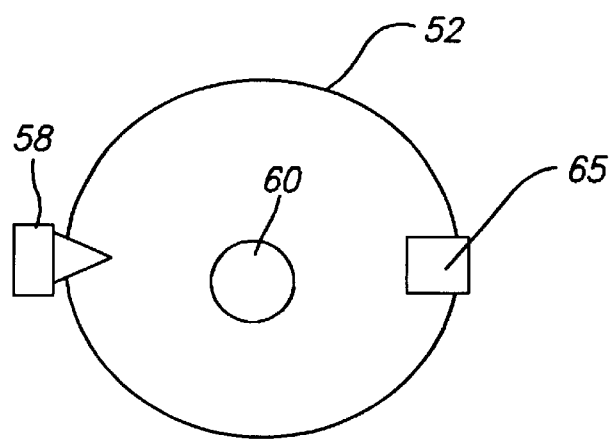
FIG. 3
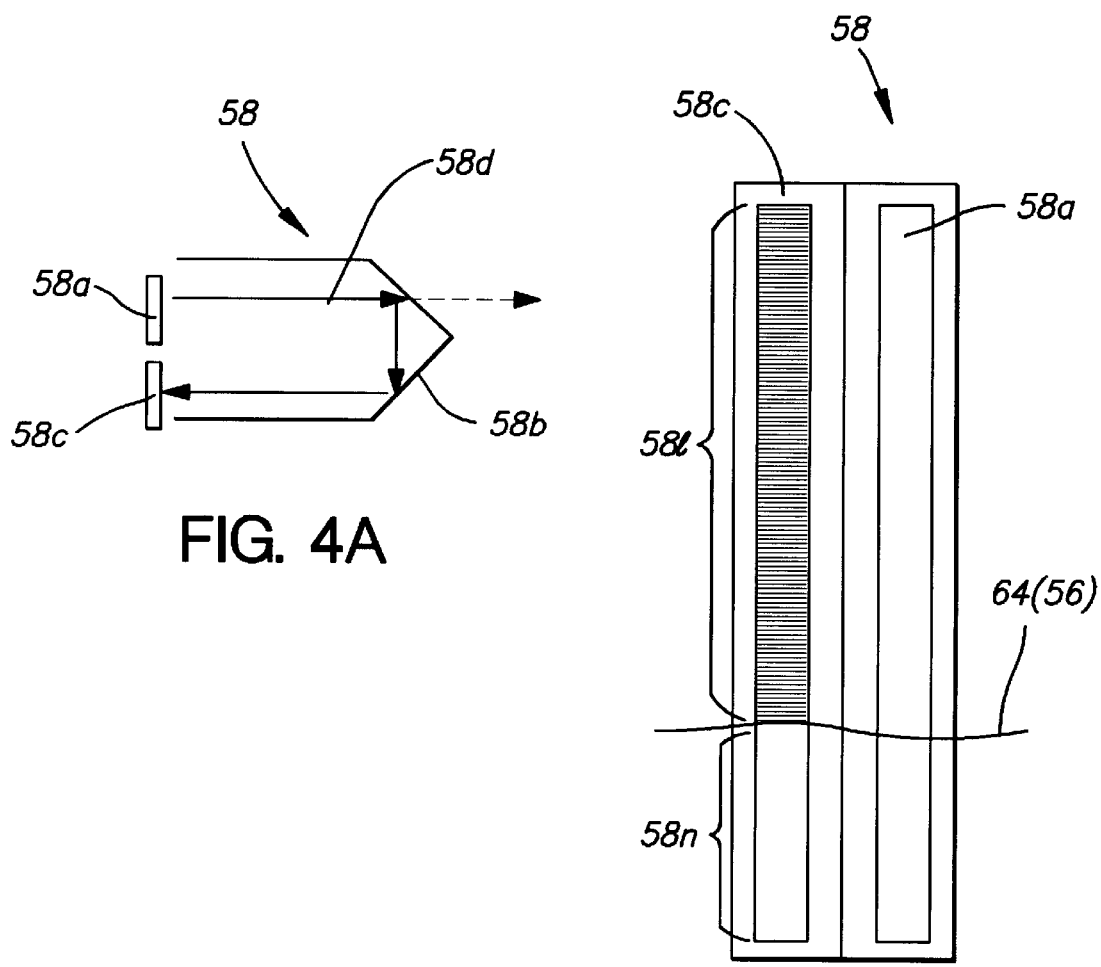
FIG. 4A
FIG. 4B

DIFFERENTIAL LEVEL HYDROMETER

FIELD OF THE INVENTION

The present invention relates to instruments used to determine specific gravity of a liquid and more particularly, to techniques and methods for automatically measuring specific gravity. Still more specifically, the present invention relates to an automatic specific gravity measuring system including a liquid level detector, a liquid temperature sensor, and a sensor for reading a coded float.

BACKGROUND AND SUMMARY OF THE INVENTION

We can identify a liquid by sensing its properties. For example, tap water flows relatively freely, has little or no flavor, and is colorless. Cooking oil flows more slowly, may have a golden or yellowish tint, and (depending on the kind of oil) may have a certain characteristic flavor and/or odor. Molasses has a still different characteristic color, odor, and taste, and is more resistant to flow.

In addition to color, odor, flavor and flow resistance, people interested in the properties of liquids are often concerned about the density of the liquid. For example, we all know that oak is more dense than balsa wood. Similarly, different liquids can have different densities. Knowing the density of a liquid is often very important.

As one example, salt water is more dense than fresh water because the dissolved salt increases the water's density. It is possible to determine the amount of salt dissolved in a solution by measuring the density of the liquid solution. It is usually most convenient to determine the density of a liquid relative to the density of pure water. This relative density is called "specific gravity." An instrument called a "hydrometer" is used to measure specific gravity.

Some non-technical people may never have heard of a hydrometer, and might think that it is a highly technical instrument found only in the laboratory. But hydrometers are actually quite common. For example, auto mechanics use a kind of hydrometer to check whether car batteries are fully charged. The mechanic inserts the hydrometer tube into the battery and withdraws a small amount of the battery acid. Small floating balls within the hydrometer tube indicate the specific gravity of the battery acid. This tells the mechanic how strong or weak the battery acid is (strong acid means a strong charge, weak acid means a weak charge).

Home hobbyists sometimes also use hydrometers. For example, people who keep salt water aquariums sometimes use a hydrometer to test how the saltiness of their aquarium water is compared with ocean water. As another example, people who brew their own beer or ferment their own wine can use a hydrometer to find out how much sugar is dissolved in the liquid. This can be useful for knowing when to stop the fermentation process, for example.

Measuring a liquid's specific gravity is also very important to some businesses. For example, it is possible to estimate the quality of crude oil by measuring its specific gravity. Lighter crude oil is good for making gasoline, butane and other light petroleum products; heavier crude oil is good for making asphalt and thick lubricating oil. The density of crude oil often determines its price. A hydrometer can be used to measure how dense (light or heavy) the crude oil is.

The basic design of laboratory hydrometers hasn't changed for a hundred years. See, for example, U.S. Pat. No. 576,537 to John Barry (1897). FIG. 1 of Mr. Barry's patent is reproduced as "prior art" FIG. 1 of this patent. The hydrometer 10 shown in Mr. Barry's patent works on the principle that a floating object displaces its weight in liquid—and will therefore float higher in liquids with greater densities. A scale 12 on Mr. Barry's hydrometer 10 indicates how high the object floats in the liquid. The scale is calibrated based on how high the object would float in pure water. One can determine the liquid's specific gravity by reading the scale to see how high the object floats in the liquid.

In more detail, prior art FIG. 1 hydrometer 10 is a sealed, graduated tube weighted at one end 14 and having a stem 16 at the other end. A graduated scale 12 is placed on or within the stem of the tube. The hydrometer 10 floats in the liquid but sinks to a depth that depends on the liquid's specific gravity. The more of stem 16 that sticks out of the liquid, the more dense the liquid. Reading the level of the liquid's surface on the stem's scale 12 indicates the liquid's specific gravity.

The prior art FIG. 1 apparatus is a "thermo-hydrometer" because it also has a thermometer 20 in the liquid. The density of a liquid can be affected by temperature. Scientists define "density" as the mass of a substance per unit volume under a specified pressure and temperature. Although changes in atmospheric pressure can generally be ignored, specific gravity is technically determined based on the density of pure water at a specific temperature (4 degrees Centigrade). To make very accurate specific gravity measurements, the scale reading must be corrected based on the temperature of the liquid being measured. Some modern hydrometers have a built-in thermometer to avoid the need for a separate thermometer.

One of the problems with the prior art FIG. 1 (or like) design is that the scale 12 on the stem 16 must be read at the air-liquid interface 22. This creates the possibility of user error. Many liquids (water, for example) tend to "wet" (stick to) the sides of both the container 24 and the sides of the hydrometer's stem 16. This means that the liquid's surface is not completely flat, but instead curves downwardly away from those surfaces to form what is called a "meniscus" (liquids that do not "wet" the container sides have an upwardly extending curved meniscus). Parallax errors and difficulties reading "through" the meniscus (especially when the liquid is not transparent) make it difficult for the user to make a correct reading. In addition to this problem, a thermo-hydrometer requires the user to read a thermometer encapsulated within the hydrometer or a separate thermometer within the liquid. This requires additional time and creates the possibility of additional user error.

In contrast, the present invention provides a differential level hydrometer that reduces the possibility for user error and provides an accurate, predictable, easy to use, reliable instrument for measuring the density (specific gravity) of a liquid.

Briefly, the differential level hydrometer provided by the present invention works by:

(a) automatically measuring the level of a liquid within a vessel;
(b) floating, in the liquid, a calibrated float having a precisely known volume and density;
(c) automatically measuring the level of the liquid within the vessel while the float is floating in the liquid; and
(d) automatically calculating the density (specific gravity) of the liquid based on the change in levels and the volume and density of the float.

In more detail, the differential level hydrometer provided in accordance with the present invention may include a vessel having known cross-sectional characteristics. The liquid the specific gravity of which is to be measured is placed into the vessel. A gravitational reference device (e.g., a bubble level or other leveling device) may be used to ensure that the vessel is precisely aligned with reference to the earth's gravitational pull. A liquid level sensor disposed within the vessel measures the "starting" level of the liquid.

Then, a float of known dimensions and density is placed into the subject liquid to be measured. When the float has been inserted into the liquid and has come to rest, the liquid level sensor measures the level the liquid has risen to. A float of a given volume and density will float higher in (and displace less volume of) more dense liquids—causing denser liquids to rise in level less than less dense liquids.

Electronics automatically calculate and display the liquid density based on the liquid's starting level, the liquid's level with the float floating in the liquid, and the dimensions and density of the float.

The following are additional features and advantages provided in accordance with various aspects of a presently preferred example embodiment of the present invention:

The float with a calibrated volume and density can be marked with electronically readable code providing the necessary data for a density calculation.

The instrument may include a device for automatically reading the code disposed on the float.

A suitable device for reading electronically encoded material (e.g., bar code or magnetic media) may be placed near the top of the open vessel to recognize the coded information on the float—thus avoiding manual user entry and associated error.

The vessel used to hold the liquid during measurement may be an open liquid vessel having a precise surface area perpendicular to the bottom of the vessel.

The open vessel should have a precision volume, but can be of any shape so long as the surface of the area of the contained liquid is uniform and perpendicular with the bottom.

A cylindrical tube shape is most likely the simplest, common volume which can be made with precise dimensions.

As one example, common laboratory glassware such as a graduated cylinder could be used for the liquid vessel.

A device may be coupled to the vessel to ensure the vessel is precisely aligned with the earth's gravitational pull (for example, a bubble level indicator may be used to ensure that the liquid surface is horizontal).

The vessel may include a liquid interface (e.g., level) sensor which is also aligned to be perpendicular to the vessel's bottom (for example, the liquid interface sensor may be placed along one vertical side of the vessel).

The instrument's liquid level interface sensor may work on optical, conductive, capacitive, sonic or other principles.

A simple optical, refractive-reflective sensor capable of determining a liquid-air interface anywhere along its length, is probably the easiest and most economical device to use. However, any sensor which can accurately determine liquid level changes will work.

The system may include a means for compensating for a meniscus that forms around the float. Although the liquid level sensor is exposed to the liquid and any meniscus remains constant throughout the level change, the meniscus which forms around the float must be compensated for (The height of the float's meniscus will vary with the properties of the subject liquid, and therefore cannot be assumed to be constant for different liquids).

By lowering the float until the bottom contacts the liquid's surface, the volume of the float meniscus can be calculated and corrected for by the level sensor and functional logic.

Other methods of meniscus correction may be made by placing gaps of known volume in the float and calculating the difference in level fluctuation as the float is lowered into the vessel.

A temperature sensor disposed within the vessel may provide a temperature signal input to make appropriate temperature correction adjustments to the specific gravity reading.

Since many liquids have their own temperature-density characteristics, the user can determine which temperature correction algorithm is best suited for the subject liquid.

Once functional logic registers the initial liquid level, the density and volume specifications of the float, the second liquid level, meniscus correction and the temperature, the logic can calculate the density (specific gravity) and display or otherwise provide this value to the user.

In the case where the user may wish to use different liquid vessels, uncoded floats, change units, choose the correct temperature algorithm, etc., a keyboard and/or computer interface may be used.

The differential level hydrometer may be made as a stand alone instrument, or it may be made to interface to a computer with appropriate hardware, or it may provide both modes.

In one example, the various sensors are attached to the liquid vessel in a manner which allows them to be easily removed. This makes the instrument easy to clean.

BRIEF DESCRIPTION OF THE DRAWINGS

These and other features and advantages provided in accordance with the present invention may be better and more completely understood by referring to the following presently preferred example embodiment in conjunction with the drawings, of which:

FIG. 3 shows an example top view of the differential level hydrometer shown in FIG. 2;

FIGS. 4A and 4B are top and side views, respectively of an example optical level reader for use in the FIG. 2 differential level hydrometer;

DETAILED DESCRIPTION OF A PRESENTLY PREFERRED EXAMPLE EMBODIMENT

Figure 1:
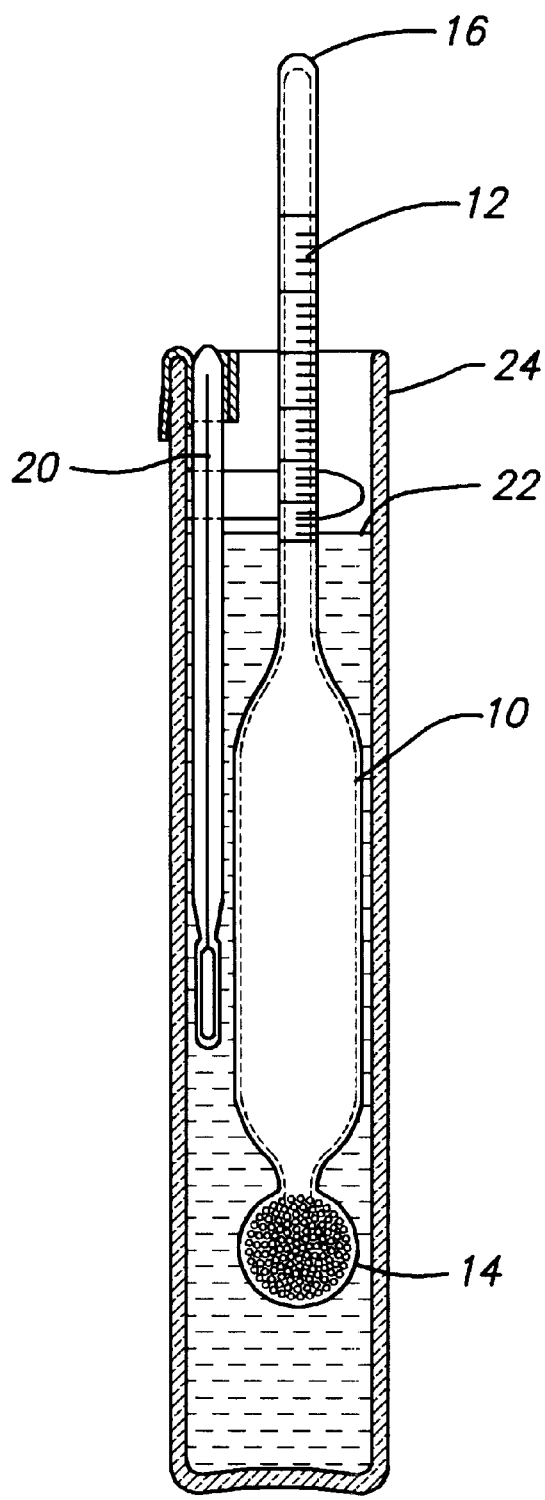
FIG. 1 shows a prior art hydrometer patented by Mr. John Barry a hundred years ago.
Figure 2:
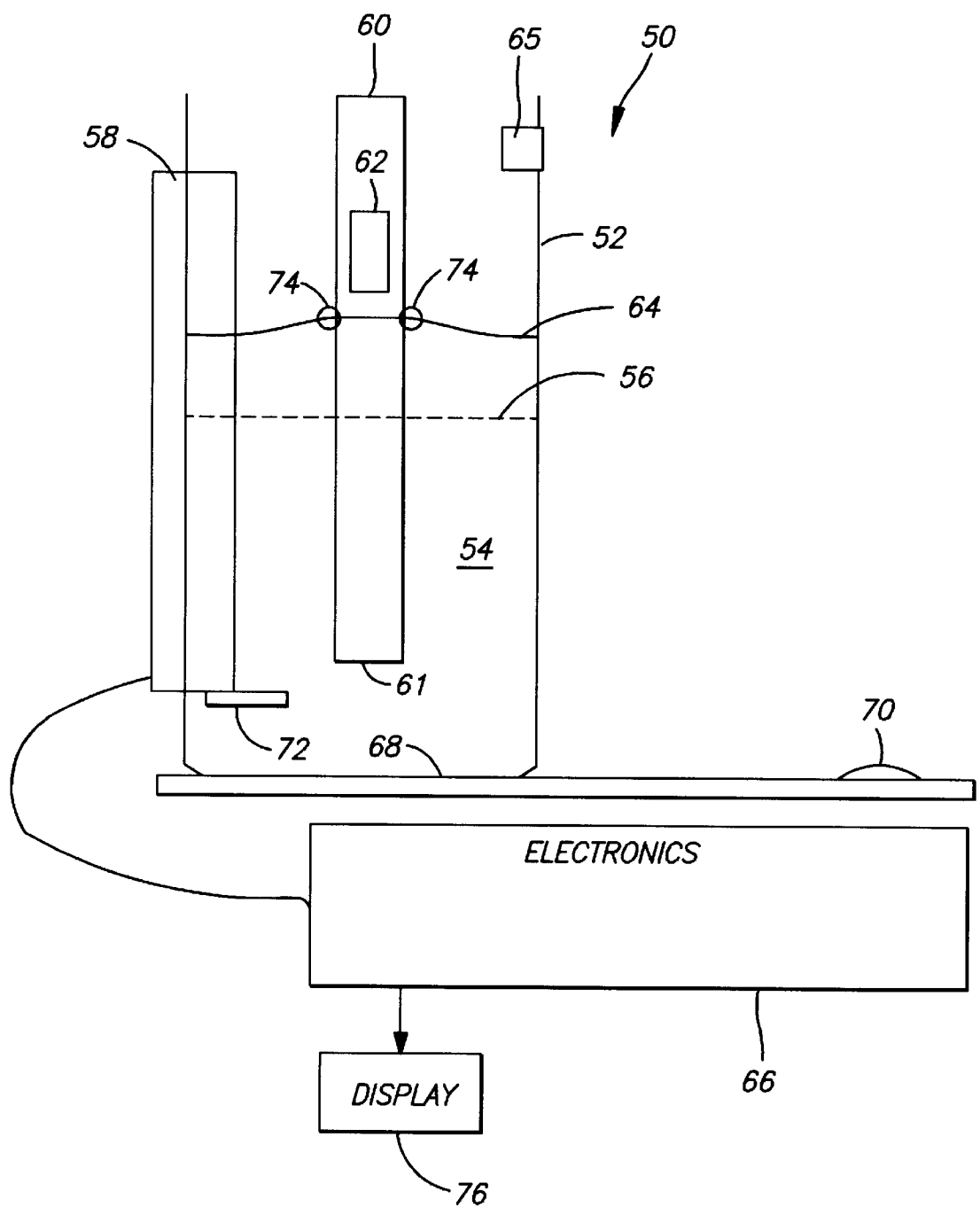
FIG. 2 shows an example differential level hydrometer provided in accordance with the present invention.

FIG. 2 shows an example embodiment of a differential level hydrometer 50 provided in accordance with the present invention. Differential level hydrometer 50 measures a difference in level of a liquid contained within a vessel 52 caused by placing a reference object 60 of known specific weight into the liquid. Hydrometer 50 calculates the liquid's specific gravity based on the measured difference in liquid level.

Differential level hydrometer 50 includes a precision open vessel 52. A subject liquid 54 the specific gravity of which is to be measured is poured into vessel 52. The initial height or level 56 of liquid 54 within vessel 52 is measured by a liquid level interface sensor 58.

A calibrated float 60 of known volume and density is then inserted into liquid 54. If desired, float 60 may include a code 62 indicating specific gravity and volume data—and this code may be automatically read by an optical or magnetic code reader 65.

Float 60 when inserted into liquid 54 displaces some of the liquid—causing the liquid level to rise within vessel 52. The amount of liquid that float 60 displaces (and thus the distance the liquid level will rise from its initial level 56) depends on the density of the liquid relative to the (known) density and volume of float 60. Float 60 will float higher in (and displace less of) a more dense liquid, and will float lower in (and displace more of) a less dense liquid.

A liquid level interface sensor measures the level 64 that liquid 54 rises to when float 60 is floating in the liquid. A temperature sensor 72 measures the temperature of liquid 54. Electronics 66 calculates the specific gravity of liquid 54 based on data it obtains from liquid level interface sensor 58, the temperature sensor 72, and code reader 65.

In this example, open liquid vessel 52 has a precise cross-sectional area perpendicular to the bottom 68 of the vessel. Precision open vessel 52 can be of any shape so long as the surface area of the contained liquid 54 is uniform and perpendicular with the bottom 68. A cylindrical tube shape is most likely the simplest, common volume which can be made easily with precision dimensions. One example of a vessel suitable for use as liquid vessel 52 is common laboratory glassware such as a graduated cylinder. A bubble balance 70 may be attached to vessel bottom 68 to ensure that the liquid vessel 52 is precisely vertically aligned relative to the earth's gravitational pull (thus ensuring that the surface area of liquid 54 is exactly perpendicular to the walls of vessel 52).

Liquid level interface sensor 58 may work on optical, conductive, capacitive, sonic, ultrasonic, laser, or other principles. In this example, liquid level interface sensor 58 can reliably measure changes in the level of liquid 54 across a range. FIGS. 4A and 4B show one example simple optical, refractive/reflective light or level sensor that can be used to determine a liquid-air interface anywhere along its length. The FIG. 4A example top view of an optical level reader 58 includes an electromagnetic source 58a, a prism 58b and a vertical sensor array 58c. Source 58a may emit light or infrared energy—infrared energy being used to minimize ambient light problems. Source 58a emits a light beam 58d toward prism 58b. The light beam is lost (i.e., the light is refracted into the liquid) if light-transmissive liquid 54 is present on that portion of prism 58b. If light-transmissive liquid 54 is not present on that portion of prism 58b, the prism reflects the light back to vertical sensor array 58c.

As shown in FIG. 4B, vertical sensor array 58c is a linear sensor array that can sense which portions 58b, of its length receive light from prism 58b, and which portions 58n of its length do not receive light from the prism. Thus, sensor array 58c measures the liquid level 64 (56) within vessel 52. Sensor array 58c in this example has sufficient individual light sensors spaced at appropriate distances along the array to provide desired accuracy and resolution.

The level sensor 58 shown in FIGS. 4A and 4B may not be suitable for opaque liquids. To measure the level of opaque liquids, a laser or ultrasonic source can be placed on the upper rim of vessel 52, the source radiates energy downward toward the liquid's surface. The liquid's surface reflects the energy back toward a sensor also disposed on the vessel 52's rim. The angle of reflection and/or the time it takes for the energy to traverse the round trip path can be sensed and used to determine the level of the liquid.

In this example, float 60 comprises an elongated cylinder of known dimensions and density. Float 60 preferably is made from a corrosion-resistant, impact-resistant, cleanable, non-absorptive material such as stainless steel, for example. Weights may be incorporated within float 60 to provide a desired density. Different floats 60 with different corresponding densities may be used to measure the specific gravity of different density liquids. For example, differential level hydrometer 50 can be sold with a number of different floats 60 having different dimensions and/or densities, or such floats could be ordered separately depending upon the customer's requirements. In general, the user should use a float 60 of appropriate dimensions and density to achieve an appreciable or maximal change in the level of liquid with and without float inserted—without, of course, the higher liquid level 64 exceeding the measuring range of level sensor 58 and/or overflowing vessel 52.

Because interchangeable floats of different dimensions and/or densities may be used, each float 60 in this example may be encoded with a machine-readable code 62 (e.g., a bar code or a magnetic strip that identifies the characteristics of the float. Code 62 provides the necessary data for the density calculation—thus avoiding manual entry of this information by the user and associated errors and inconvenience such manual entry may cause.

Differential level hydrometer 50 shown in FIG. 2 includes a code reader 65 that automatically reads codes 62 disposed on float 60. For example, code 62 might indicate the dimensions of the float 60 and its density—or it may provide an identification number or other indicia that electronics 66 can use to look up the characteristics of the float in a reference database. Although differential level hydrometer 50 can function without code reading device 65, the use of the code reading device eliminates the possibility of entry errors and facilitates faster results.

In this example, temperature sensor 72 within vessel 52 measures the temperature of liquid 54 and provides the measured temperature information to electronics 66. Since different liquids have different temperature-density characteristics, it is necessary for electronics 66 (or the user) to determine which correction algorithm is best suited for the subject liquid 54. Temperature correction information can be obtained from a variety of different sources such as, for example, the American Petroleum Institute (API) and the American Society for Testing and Materials (ASTM).

The liquid surface level 64 will exhibit a meniscus the shape of which depends on the characteristics of the subject liquid 54. The shape and volume of the meniscus formed on level sensor 58 and on the walls of vessel 52 (due to the degree of wetting or non-wetting) of level sensor 58 for each of the two liquid levels 56, 64 will be the same. Therefore, the meniscus caused by level sensor 58 and vessel 52 itself is automatically compensated for. However, the meniscus 74 that forms around float 60 must be compensated for because it effectively takes away a volume of liquid 54 that would otherwise contribute to level 64.

The height of meniscus 74 will vary with the properties of the subject liquid 54, and cannot be assumed to be constant. One way to compensate for meniscus 74 is to lower the float 60 until the float bottom 61 contacts liquid surface 56. The volume of the meniscus can be calculated and corrected for by level sensor 58 and electronics 66. Other methods of meniscus correction may be used (e.g., by placing gaps of known volume in the float 60 and calculating the difference in level fluctuation as the float is lowered into the vessel, or by inputting or storing and reporting compensation information measured previously based on the same or similar float in the same or similar liquid).

In this example, electronics 66 calculates the specific gravity of liquid 54 based on the inputs it receives from the various sensors and other information. Electronics 66 may, for example, include a sensor interface, operational logic, a keyboard or personal computer interface to enter hydrometer-float data or correction factors, SP or API units, etc. Electronics 66 may output the specific gravity value it calculates to a display 76, a printer, etc.

In more detail, electronics 66 may calculate liquid density based on the cross-sectional area of vessel 52, the initial level 56 of the subject liquid 54, the final level 64 of the subject liquid, and the precise volume and density of the float (reference object) 60. In addition, electronics 66 may apply a temperature correction factor based on the temperature of the subject liquid 54. Electronics 66 registers the initial liquid level 56 measured by level sensor 58, the density and volume specifications of float 60 (e.g., as indicated by the code 62 read by code reader 65), the second liquid level 64 after float has been inserted into the liquid, and the liquid temperature measured by temperature sensor 72. Based on these various sensor inputs, electronics 66 calculates the density (specific gravity) of liquid 54 and displays it on a visual display 76 for the user. As discussed above, electronics 66 preferably also corrects the measurement for the meniscus 74 which forms around float 60.

If desired, user input devices (e.g., a keyboard and/or computer interface) may be provided in the case where the user wishes to use different liquid vessels 52, uncoded floats 60, change units, choose temperature correction algorithms, or otherwise influence or customize the measurement. Differential level hydrometer 50 may thus be made as a stand-alone instrument, an instrument for interfacing with a computer with appropriate software, or may operate in either or both modes.

Figure 5:
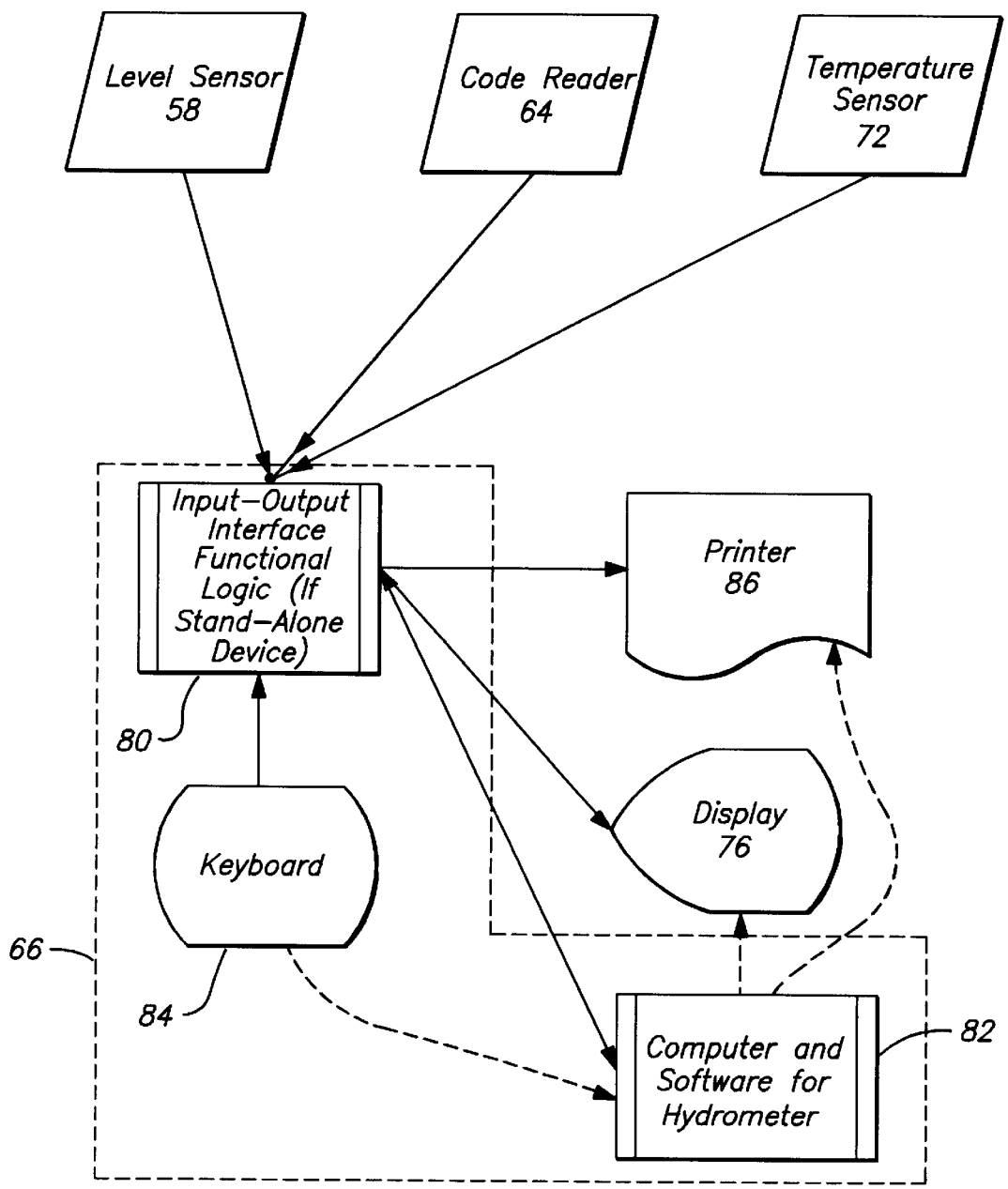
FIG. 5 shows an example block diagram of a differential level hydrometer measuring system.

FIG. 5 shows one example overall block diagram of hydrometer 50 in which level sensor 58, code reader 65 and temperature sensor 72 each provide their outputs to an input-output interface functional logic 80. Logic 80 (which may be hard-wired digital logic circuitry and/or an appropriately programmed microcomputer) may cooperate with a conventional personal or other computer 82 programmed with appropriate computer software. As mentioned above, a keyboard 84 can provide user-variable inputs to logic 80 and/or computer 82. Logic 80 and/or computer 82 may calculate specific gravity and provide the calculated value (as well as other values) to display 76 and/or a printer 86.

Figure 6:
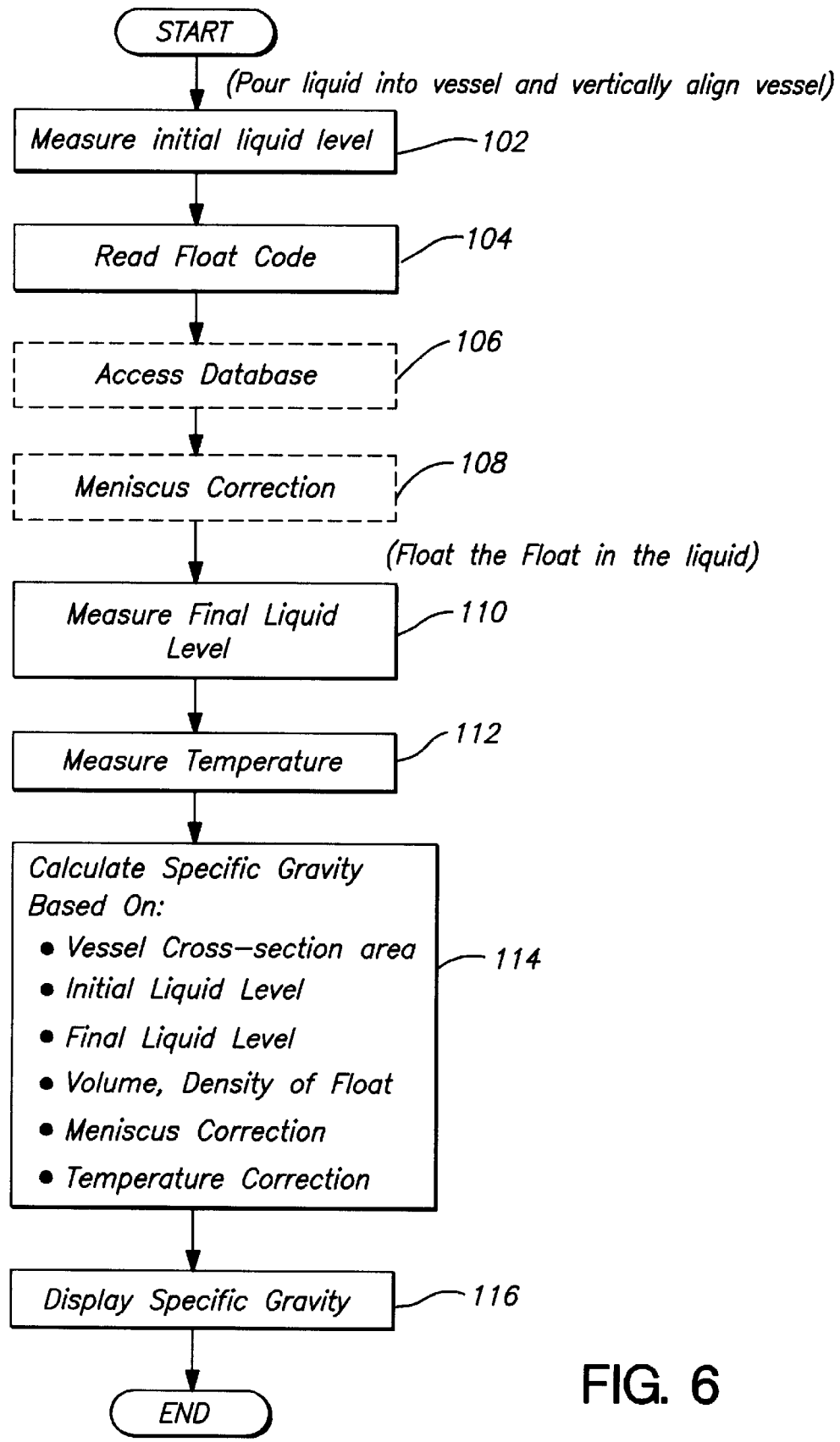
FIG. 6 shows a flowchart of example program control steps performed by the FIG. 5 arrangement.

FIG. 6 shows an example process for measuring specific gravity of a subject liquid 54. The user first pours a desired amount of the subject liquid into vessel 52 and initiates a measuring sequence (e.g., by depressing a button or other user control associated with electronics 66). In response, electronics 66 measures the initial liquid level 56 by reading and storing the output of level sensor 58 (block 102). The user next passes the float code 62 in proximity with code reader 65, and electronics 66 reads the float code (block 104). Float code reading may, for example, provide audible and/or visual feedback to the user that electronics 66 has successfully read the float code or needs to try again. If necessary, electronics 66 accesses a database containing float characteristics based on the float code read by code reader 65 (block 106).

Electronics 66 may next perform a meniscus correction calculation (block 108) to correct for the meniscus 74 which forms around the float. As one example, the user may lower float 60 until its bottom 61 contacts vessel bottom 68, and then depresses a button to initiate electronics 66 to measure the new level of liquid 54 by reading level sensor 58. Electronics 66 may, based on this changed level and known dimensions of float 60, calculate a correction factor to correct for meniscus 74.

The user next floats float 60 in the liquid and allows the float to come to rest so that it is floating in nearly the center of the vessel 52 (see FIG. 3). The user may then depress another control to cause electronics 66 to measure the final liquid level 64 (block 110). Electronics 66 may then measure the temperature of liquid 54 by sensing the output of temperature sensor 72 (block 112). Electronics 66 then calculates the specific gravity (density) of liquid 54 based on:

the cross-sectional area of vessel 52,
initial liquid level 56,
final liquid level 64,
the volume and density of float 60,
meniscus correction, and
temperature correction.

Electronics 66 may display a calculated specific gravity value on display 76 for the user (block 116).

The following is a brief discussion of the theory of operation for the specific gravity calculation performed by block 114 of FIG. 6:

$$\text{Buoyant Force} = \text{Density} \times \text{Volume of Displaced Liquid } (B = \rho V) \quad \text{(Equation 1)}$$

When materials of different density (specific gravity) are in equilibrium, then the sum of all forces is zero.

$$0 = B = \rho_1 V_1 - \rho_2 V_2 \quad \text{(Equation 2)}$$

This means that:

$$\rho_1 V_1 = \rho_2 V_2 \quad \text{(Equation 3)}$$

Using the above relationship, and a vessel with a uniform cross-section and vertical walls, the density of a liquid (specific gravity) within the vessel can be determined. The following constants must be known:

Area of the vessel Cross Section
Initial level of subject liquid
Final level of subject liquid
Precise volume of the reference object
Precise density of the reference object.
Plugging values into equation (3) above:

$$\text{Density}_1(\text{Area} \times \text{Height}) = \text{Density}_2(\text{Area} \times \text{Height}) \quad \text{(Equation 4)}$$

Let $\rho_1 V_1$ be the known reference density and volume. Then:

$$\rho_1 V_1 = (\rho_2)(\text{Area})(\text{Height}) \quad \text{(Equation 5a)}$$

$$\rho_1 V_1 = (\rho_2)(\text{Area})(\text{Level2} - \text{Level1}) \quad \text{(Equation 5b)}$$

$$\rho_2 = \rho_1 V_1 / (\text{Area})(L_2 - L_1) \quad \text{(Equation 5c)}$$

For example, suppose:

$\rho_1 = 31.2 \text{ lb/ft}^3$, $V_1 = 0.00908 \text{ ft}^3$,

Area $= 0.0654 \text{ ft}^2$, and $(L_2 - L_1) = 0.0791$ ft.

Then, substituting into Equation 5c:

$(31.2 \text{ lb/ft}^3)(0.00908 \text{ ft}^3)/0.0654 \text{ ft}^2 (0.0791 \text{ ft}) = \rho_2$;

$\rho_2 = 54.65 \text{ lb/ft}^3$.

To correct for density variations due to temperature, a temperature sensor and appropriate algorithm will be used.

A differential level hydrometer and associated method have been described which are reliable, easy to use, and provide accurate indications of the specific gravity of a liquid. The measurements are convenient and save the user time and reduce errors. The resulting specific gravity values are useful for a wide variety of applications including but not limited to a petroleum analysis, water salinity analysis, wine and beer making, and many other uses.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of measuring the density of a liquid within a vessel comprising:
   (a) automatically measuring the level of the liquid within the vessel;
   (b) placing a calibrated reference object into the liquid;
   (c) automatically measuring the level of the liquid within the vessel while the reference object is disposed in the liquid;
   (d) automatically providing a temperature measurement signal that indicates the temperature of the liquid; and
   (e) automatically calculating the density of the liquid based on the levels measured by steps (a) and (c) and also based on at least one known characteristic of the calibrated reference object and further based on said temperature signal to make appropriate temperature correction to the calculated density.

2. A method as in claim 1 further including the step of selecting the reference object based on characteristics that provide sufficient displacement and associated change of liquid level to provide a repeatable density measurement.

3. A differential level hydrometer including:
   a vessel having known cross-sectional characteristics, the vessel for accepting and holding liquid the density of which is to be measured;
   a reference object having known characteristics for, in use, being placed into the liquid;
   a liquid level sensor disposed within the vessel for making a first measurement of the level of the liquid within the vessel without the reference object being disposed in the liquid, and for making a second measurement of the level of the liquid within the vessel while the reference object is disposed in the liquid;
   a temperature sensor disposed within the vessel, said temperature sensor providing a temperature signal; and
   electronics coupled to at least the liquid level sensor for automatically calculating liquid density based on the first and second level measurements and the characteristics of the reference object and for automatically correcting the calculated liquid density based on said temperature signal.

4. A differential level hydrometer as in claim 3 further including a gravitational reference device physically coupled to the vessel for helping to ensure that the vessel is precisely aligned with reference to the earth's gravitational pull.

5. A differential level hydrometer as in claim 3 wherein the reference object comprises a float that floats in the liquid.

6. A differential level hydrometer as in claim 3 further including a display coupled to the electronics, the display displaying the liquid density.

7. A differential level hydrometer as in claim 3 wherein the vessel comprises a graduated cylinder.

8. A differential level hydrometer as in claim 3 wherein the level sensor includes an elongated light sensor array.

9. A differential level hydrometer as in claim 3 wherein the reference object comprises a calibrated, elongated, cylindrical float made from a corrosion-resistant, impact-resistant, non-porous material.

10. A differential level hydrometer as in claim 3 wherein the electronics includes a personal computer.

11. A differential level hydrometer as in claim 3 wherein the electronics includes operational logic that calculates specific gravity.

12. A differential level hydrometer including:
    a vessel having known cross-sectional characteristics, the vessel for accepting and holding liquid the density of which is to be measured;
    a reference object having known characteristics for, in use, being placed into the liquid;
    a liquid level sensor disposed within the vessel for making a first measurement of the level of the liquid within the vessel without the reference object being disposed in the liquid, and for making a second measurement of the level of the liquid within the vessel while the reference object is disposed in the liquid; and
    electronics coupled to at least the liquid level sensor for automatically calculating liquid density based on the first and second level measurements and the characteristics of the reference object,
    wherein the reference object has a machine-readable indicia disposed thereon, and the hydrometer further includes means for automatically reading said indicia.

13. A differential level hydrometer including:
    a vessel having known cross-sectional characteristics, the vessel for accepting and holding liquid the density of which is to be measured;
    a reference object having known characteristics for, in use, being placed into the liquid;
    a liquid level sensor disposed within the vessel for making a first measurement of the level of the liquid within the vessel without the reference object being disposed in the liquid, and for making a second measurement of the level of the liquid within the vessel while the reference object is disposed in the liquid; and
    electronics coupled to at least the liquid level sensor for automatically calculating liquid density based on the first and second level measurements and the characteristics of the reference object, wherein the electronics includes means for compensating for a meniscus that forms around the reference object when the reference object is placed in the liquid.

14. A differential level hydrometer including:

a vessel having known cross-sectional characteristics, the vessel for accepting and holding liquid the density of which is to be measured;

a reference object having known characteristics for, in use, being placed into the liquid;

a liquid level sensor disposed within the vessel for making a first measurement of the level of the liquid within the vessel without the reference object being disposed in the liquid, and for making a second measurement of the level of the liquid within the vessel while the reference object is disposed in the liquid; and electronics coupled to at least the liquid level sensor for automatically calculating liquid density based on the first and second level measurements and the characteristics of the reference object, wherein the level sensor includes an electromagnetic source, an electromagnetic sensor, and a prism, the prism selectively reflecting or refracting electromagnetic energy from the source depending on whether the liquid is in contact with the prism.

15. A method of measuring the specific gravity of a liquid, the method comprising:

(a) pouring the liquid into a vessel having a known cross-section;

(b) using a gravitational reference to ensure that the vessel is precisely aligned with reference to the earth's gravitational pull;

(c) automatically, electronically measuring the level of the liquid within the vessel and producing a first electrical signal indicating said liquid level;

(d) placing a float of known dimensions and density into the liquid;

(e) automatically, electronically measuring the liquid level while the float is floating in the liquid and producing a second electrical signal indicating said liquid level while the float is floating in the liquid;

(f) automatically measuring the temperature of the liquid within the vessel and producing a third electrical signal indicating said liquid temperature; and using a digital circuit to automatically calculate the specific gravity of the liquid based on the levels indicated by said first and second electrical signals, the liquid temperature indicated by said third electrical signal, and further based on the dimensions and density of the float, to provide a calculated, temperature-compensated specific gravity indication for said liquid.

16. A method as in claim 15 wherein the step of using a digital circuit includes selecting a temperature correction algorithm based on the type of liquid.

17. A method as in claim 15 wherein each of steps (c) and (e) includes generating an electromagnetic beam.

18. A method of measuring the specific gravity of a liquid, the method comprising:

(a) pouring the liquid into a vessel having a known cross-section;

(b) using a gravitational reference to ensure that the vessel is precisely aligned with reference to the earth's gravitational pull;

(c) measuring the level of the liquid within the vessel;

(d) placing a float of known dimensions and density into the liquid;

(e) measuring the liquid level while the float is floating in the liquid; and (f) calculating the specific gravity of the liquid based on the levels measured by steps (c) and (e) and further based on the dimensions and density of the float, further including the step of machine reading a code disposed on said float, and wherein the calculating step (e) includes determining the dimensions and density of the float based on said read code.

19. A method of measuring the specific gravity of a liquid, the method comprising:

(a) pouring the liquid into a vessel having a known cross-section;

(b) using a gravitational reference to ensure that the vessel is precisely aligned with reference to the earth's gravitational pull;

(c) measuring the level of the liquid within the vessel;

(d) placing a float of known dimensions and density into the liquid;

(e) measuring the liquid level while the float is floating in the liquid; and (f) calculating the specific gravity of the liquid based on the levels measured by steps (c) and (e) and further based on the dimensions and density of the float, further including the step of correcting said specific gravity for a meniscus formed around the float.

* * * * *